United States Patent
Grivas et al.

[11] Patent Number: 6,096,081
[45] Date of Patent: *Aug. 1, 2000

[54] DIAPHYSIAL CORTICAL DOWEL

[75] Inventors: Nicholas E. Grivas, Charlotte, N.C.; Jamie M. Grooms; Kevin Carter, both of Alachua, Fla.; David Dulebohn, Naples, Fla.

[73] Assignee: University of Florida Tissue Bank, Inc., Alachua, Fla.

[*] Notice: This patent is subject to a terminal disclaimer.

[21] Appl. No.: 09/101,903
[22] PCT Filed: Jan. 16, 1997
[86] PCT No.: PCT/US97/00630
§ 371 Date: Jul. 16, 1998
§ 102(e) Date: Jul. 16, 1998
[87] PCT Pub. No.: WO97/25945
PCT Pub. Date: Jul. 24, 1997

Related U.S. Application Data

[63] Continuation-in-part of application No. 08/587,070, Jan. 16, 1996, Pat. No. 5,814,084.

[51] Int. Cl.[7] .................................................. A61F 2/44
[52] U.S. Cl. ....................... 623/17.11; 623/901; 606/79
[58] Field of Search ................... 623/16, 17, 66, 623/901; 606/79, 80, 95, 96

[56] References Cited

U.S. PATENT DOCUMENTS

| | | |
|---|---|---|
| 3,848,601 | 11/1974 | Ma et al. . |
| 4,293,962 | 10/1981 | Fuson .......................................... 606/95 |
| 4,743,146 | 5/1988 | Khmelnitsky et al. . |
| 4,856,503 | 8/1989 | Schelhas . |
| 4,877,020 | 10/1989 | Vich . |
| 4,878,915 | 11/1989 | Brantigan . |
| 4,950,296 | 8/1990 | McIntyre . |
| 5,015,247 | 5/1991 | Michelson . |
| 5,015,255 | 5/1991 | Kuslich . |
| 5,171,279 | 12/1992 | Mathews . |
| 5,458,638 | 10/1995 | Kuslich . |
| 5,662,657 | 9/1997 | Carn ........................................... 606/95 |
| 5,766,253 | 7/1998 | Brosnahan . |
| 5,814,084 | 9/1998 | Grivas et al. ............................... 623/16 |

FOREIGN PATENT DOCUMENTS

| | | |
|---|---|---|
| 0 077 159 | 4/1983 | European Pat. Off. . |
| 0 307 241 | 3/1989 | European Pat. Off. . |
| WO 95/19797 | 7/1995 | WIPO . |

*Primary Examiner*—Mickey Yu
*Assistant Examiner*—Choon P. Koh
*Attorney, Agent, or Firm*—Bencen & Van Dyke, P.A.; Gerald H. Bencen, Esq.; Timothy H. Van Dyke, Esq.

[57] ABSTRACT

A dowel (300) is provided by obtaining a plug from the shaft (diaphysis) of various long bones. The dowel (300) has an intra-medullary canal (30) which can be packed with any of a variety of osteogenic materials. The dowel (300) has a cortical surface (10) into which an instrument attachment hole (15) may be machined and onto which an alignment mark (16) may be inscribed for proper orientation of the intra-medullary canal (30) or a driver slot (56) which may be used to assist in further machining of the bone dowel (300). The dowel (300) ha a chamfered insertion end and has improved biomechanical and vertebral fusion induction properties as compared to standard dowels known in the art. A threaded (31) or grooved (32) dowel (300) and an apparatus (400) for efficient production thereof are also provided.

41 Claims, 14 Drawing Sheets

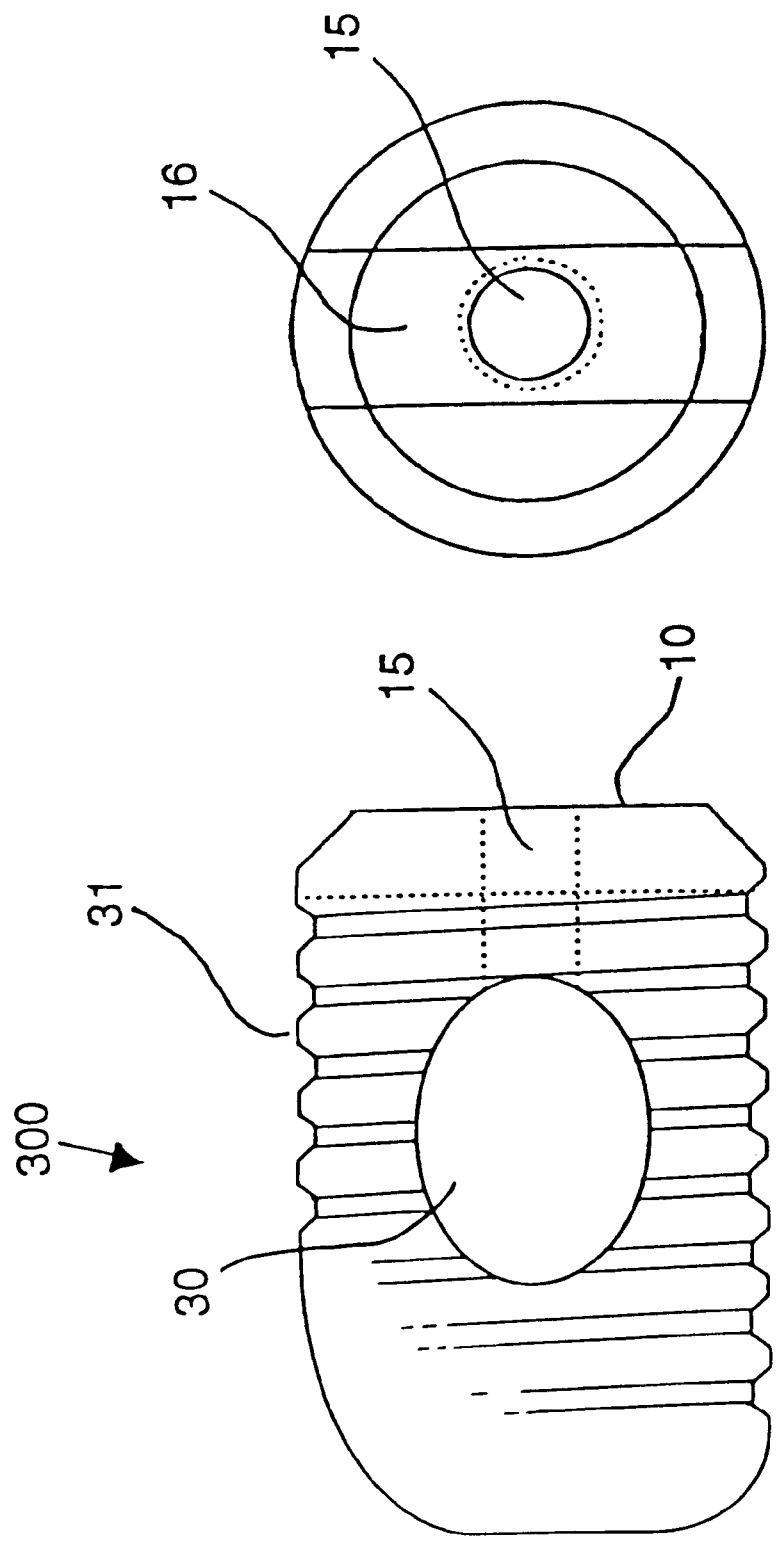

DIAPHYSIAL CORTICAL DOWEL

This application is a continuation-in-part of U.S. application Ser. No. 08/587,070, filed Jan. 16, 1996, U.S. Pat. No. 5,814,084.

BACKGROUND OF THE INVENTION

1. Field of the Invention

The invention provides a novel dowel machined from the cortex of bone diaphyses and methods of use thereof.

2. Background

It is common for patients presenting with spinal trauma or pathology to require the fusion of two or more vertebra. In the art, a standard solution to this problem is to create a cavity between two adjacent vertebra to accept the insertion of a dowel made from bone or another material. For this purpose, a dowel known as the Cloward Dowel has been in use for many years. That device is a generally circular pin made by drilling an allogeneic or autogenic plug from the cancellous bone of the ilium (i.e., the hip bone). As such, this bone has two cortical surfaces (i.e., it is bicortical) and has an open, latticed or porous structure between the two cortical surfaces. Unfortunately, such dowels have very poor biomechanical properties, principally being susceptible to compression. Accordingly, such dowels present the major danger of collapsing prior to fusion of the adjacent vertebra between which such a dowel is inserted.

A dowel of greater biomechanical properties has been produced from allogeneic femoral or tibial condyles (i.e., the rounded prominence at the end of the femur or tibia where such bones articulate with other bones). The result of drilling a plug from such a condyle is a unicortical dowel. Such unicortical dowels are available from most tissue banks, including the University of Florida Tissue Bank, Inc. (see, for example, our Allograft Catalog, product numbers 280012, 280014, and 280016; this catalog and these products are available on request by calling 904-462-3097, or by calling 1-800-OAGRAFT, or by writing to the University of Florida Tissue Bank, Inc. 1 Progress Boulevard, P.O. Box 31, S. Wing, Alachua, Fla. 32615). While such unicortical dowels represent a major advance over the bicortical dowels of Cloward, desribed above, from a biomechanical point of view, the biomechanical properties of the diaphysial cortical dowel of the instant invention is expected to represent a substantial improvement over the unicortical dowels, due to the greater density of source bone, as will be evident from a reading of the full disclosure which follows.

In addition to the known Cloward and unicortical dowels, a number of U.S. Patents have been found dealing with the general area of dowels for achieving vertebral fusions. Thus, for example, U.S. Pat. No. 5,015,247 discloses a threaded spinal implant which, when placed between two adjacent vertebrae, directly participates and is incorporated in the ensuing fusion. The implant is made of a hollow metal casing which is filled with osteogenic material. A plurality of perforations are provided in the casing so that bone can grow into and out of the implant. Metal threads and tabs are provided to insert and prevent backing out of the implant, respectively. However, the implant is made out of metal and thus is a foreign object which is inserted into the spine and is thus never fully incorporated into the fusion. Furthermore, as the implant is preferably made of titanium, production of the implant requires the use of specialized metal molding and machining, and production of the implant material itself, which is expensive.

In U.S. Pat. No. 4,627,853, a method of producing a prosthesis for replacement of articular cartilage and the prostheses so produced is disclosed. The prostheses of the '853 patent, principally designed for articulating cartilage replacement, are machined from allogenic or xenogeneic bones segments and then demineralized to produce a bone fragment with a spongy texture similar to natural cartilage. The prostheses are also tanned to render the material non-antigenic. While the methods of the '853 patent may be used to alter the properties of the diaphysial cortical dowel of the instant invention, and the disclosure of the '853 patent is herein incorporated by reference for that purpose, the '853 patent does not teach or suggest the novel device and method of the instant invention.

In U.S. Pat. No. 5,053,049, a flexible prosthesis and a method for making such prostheses are disclosed. The process includes machining a bone, demineralizing the bone to impart a desired degree of flexibility, and tanning to render the material non-antigenic. This patent is generally similar in disclosure to the disclosure found in the '853 patent discussed above, except that the particular applicability of the disclosed process to the production of an outer ear prosthesis is emphasized.

In U.S. Pat. No. 5,306,303, a bone induction method is disclosed which consists of implanting a bone morphogenetic, protein-free ceramic in the soft tissue or bone of an animal. The ceramic disclosed as preferable is calcium phosphate and the use of such material for achieving spinal intervertebral joint fusions (disk arthroplasty) is suggested. The material and product of the '303 patent, aside from its possible use for a purpose similar to that for which the instant product is designed, bears little or no resemblance to the instant invention.

In U.S. Pat. No. 5,171,279, a method for subcutaneous suprafascial pedicular internal fixation of vertebrae of the spine is disclosed to facilitate graft fusion. The method included excision of the nucleous of an affected disc, preparation of a bone graft, instrumentation of the vertebrae for fixation, and introduction of a bone graft into the resected nuclear space. Metallic fixation hardware is disclosed as the principal aspect of the claimed invention. Accordingly, aside from dealing with the same general problem, the invention disclosed and claimed in the '279 patent bears little resemblance to the diaphysial cortical dowel and method of the instant invention.

Accordingly, having reviewed many solutions attempted in the field prior to the instant disclosure, it is concluded that there remains the need for a vertebral fusion graft which has superior biomechanical and vertebral fusion promoting properties. The instant invention provides such a graft as well as a method for making and using the graft.

BRIEF SUMMARY OF THE INVENTION

The diaphysial cortical dowel of this invention is a graft useful in cervical or thoracic and lumbar fusions. For cervical fusions, the dowel is preferably obtained from the allogeneic fibula, radius, ulna and occasionally, from small humeri. The dimensions of such dowels are typically between about 8–15 mm in length (depth) and about 10–14 mm in diameter. For thoracic and lumbar fusions, the dowel is preferably obtained from the humerus, femur or tibia. The dimensions of such dowels are typically between about 10–30 mm in length (depth) and about 14–20 mm in diameter. In each case, the dowel is obtained as a transverse plug from the diaphysis of these bones. Accordingly, each dowel has the feature of having the natural intra-medullary canal of the source bone forming a cavity through the dowel, perpendicular to the length of the dowel, which can be prepacked with allogeneic cancellous bone, autogenous bone fragments, hydroxyapatite, bioglass, mixtures of these elements or any other bioceramic or osteogenic material to promote rapid fusion of the vertebrae between which the dowel is inserted. Such dowels are generally referred to herein as "diaphysial" cortical dowels. Unlike prior bone grafts, the present invention provides a generally cylindrical dowel of cortical bone having a canal through the dowel generally perpendicular to the long axis of the dowel.

The method of for preparing and using the diaphysial cortical dowel of this invention comprises the steps of obtaining a plug from the diaphysis of an appropriate donor bone or a plug from an alternate acceptable cortical bone source through which a perpendicular canal may be machined. Typically, the donor will have been extensively screened for communicable diseases, cancer, and at-risk behavior prior to acceptance of the donor bone for dowel formation. The plug is then machined, preferably in a class 10 clean room, to the dimensions desired. Optionally, a groove is inscribed on the circumference of the dowel to prevent backing-out of the dowel. Another option is to inscribe a thread onto the cylindrical surface (circumference) of the dowel to improve fixation and prevent backing out. Chamfering of the forward end of the dowel which is to be inserted into a cavity formed between adjacent vertebrae is also preferred. The curvature of the chamfered end aids in the ease of insertion. Preferably, an instrument attachment hole is machined in the opposite end of the dowel from the chamfered end. Preferably, a score mark is inscribed on the cortical end into which the instrument attachment hole is machined so that the surgeon can align the intra-medullary canal so that the canal is parallel with the length of the recipient's spatial column.

In use, the surgeon creates a cavity between two adjacent vertebra that are to be fused. The autogenous bone fragments may be collected and packed into the intra-medullary canal of the diaphysial cortical dowel, or the dowel may be used with a pre-packed osteogenic composition. The dowel is mounted on an instrument via the instrument attachment hole and carefully inserted into the cavity created between the adjacent vertebrae to be fused. Over a period of several months, it is found that substantial fusion of the adjacent vertebrae occurs.

Accordingly, it is one object of this invention to provide a diaphysial cortical dowel made from bone for insertion between vertebrae to be fused.

Another object is to improve patient incidence of safe and satisfactory fusion.

Another object of this invention is to provide a dowel for vertebral fusion which has improved biomechanical properties over standard Cloward Dowels and unicortical dowels known in the art.

Another object of this invention is to provide a dowel with improved osteogenic and vertebral fusion promoting capacity.

Another object of this invention is to provide a dowel with a natural canal running therethrough to accept packing having ostogenic properties.

Another object of this invention is to provide a method for making a novel diaphysial cortical dowel.

Another object of this invention is to provide a method for using the novel diaphysial cortical dowel of this invention.

Additional objects and advantages of the diaphysial cortical dowel of this invention will become apparent from the full disclosure which follows.

BRIEF SUMMARY OF THE FIGURES

FIGS. 3A and 3B depict one embodiment of this invention in which the dowel is threaded.

DETAILED DESCRIPTION OF THE INVENTION

Figure 1A:
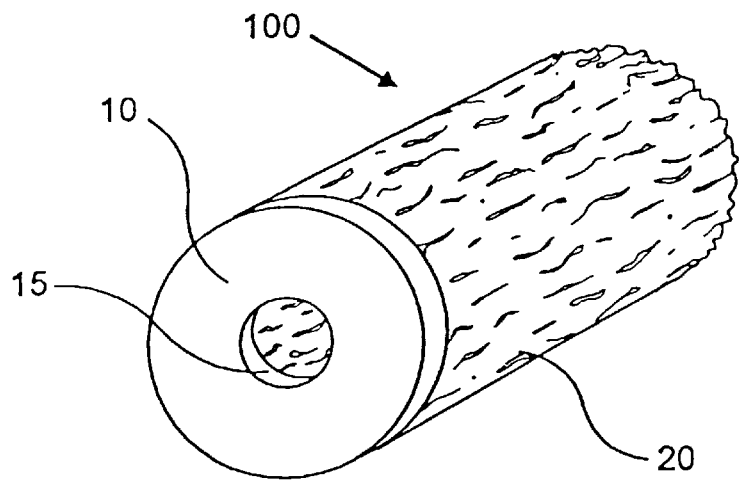
FIG. 1A depicts the structure of a standard unicortical dowel known in the art.

The diaphysial cortical dowel of this invention is a graft useful in cervical or thoracic and lumbar fusions. For cervical fusions, the dowel is preferably obtained from the fibula, radius, ulna and occasionally, from small humeri. The dimensions of such dowels are typically between about 8–15 mm in length (depth) and about 10–14 mm in diameter. For thoracic and lumbar fusions, the dowel is preferably obtained from the humerus, femur or tibia. The dimensions of such dowels are typically between about 10–30 mm in length (depth) and about 14°mm in diameter. In each case, the dowel is obtained as a transverse plug from the diaphysis of these long bones. Preferably, the bone plugs are obtained using a diamond or hard metal tipped cutting bit which is water cleaned and cooled. Commercially available bits (e.g. core drills) having a generally circular nature and an internal vacant diameter between about 10 mm to about 20 mm are amenable to use for obtention of these bone plugs. Such core drills are available, for example, from Starlite, Inc. A machine for obtention of endo- and cortical dowels consists of a pneumatic driven miniature lathe which is fabricated from stainless steel and anodized aluminum. It has a spring loaded carriage which travels parallel to the cutter. The carriage rides on two runners which are 1.0 inch (2.54 cm) stainless rods and has a travel distance of approximately 8.0 inches (20.32 cm). One runner has set pin holes on the running rod which will stop the carriage from moving when the set pin is placed into the desired hole. The carriage is moveable from side to side with a knob which has graduations in metric and in English. This allows the graft to be positioned. On this carriage is a vice with clamps the graft and holds it in place while the dowel is being cut. The vice has a cut out area in the jaws to allow clearance for the cutter. The lathe has a drive system which is a pneumatic motor with a valve controller which allows a desired RPM to be set.

First, the carriage is manually pulled back and locked in place with a set pin. Second, the graft is loaded into the vice and is aligned with the cutter. Third, the machine is stared and the RPM is set by using a knob on the valve control. Fourth, the set pin, which allows the graft to be loaded onto the cutter to cut the dowel. Once the cutter has cut all the way through the graft the carriage will stop on a set pin. Fifth, sterile water is used to eject dowel out of the cutter. It is fully autoclavable and has a stainless steel vice and/or clamping fixture to hold grafts for cutting dowels. The graft can be positioned to within 0.001" (0.3 mm) of an inch which creates dowel uniformity during the cutting process.

The cutter used in conjunction with the above machine can produce dowels ranging from 5 mm to 30 mm diameters and the sizes of the cutters are 10.6 mm; 11.0 mm; 12.0 mm; 13.0 mm; 14.0 mm; 16.0 mm; and 18.0 mm. The composition of the cutters is stainless steel with a diamond powder cutting surface which produces a very smooth surface on the wall of the dowels. In addition, sterile water is used to cool and remove debris from graft and/or dowel as the dowel is being cut (hydro infusion). The water travels down through the center of the cutter to irrigate as well as clean the dowel under pressure. In addition, the water aides in ejecting the dowel from the cutter.

Plugs having a depth of about 8 mm to about 30 mm are, generally acceptable, with appropriate gradations in length and diameter naturally being available at the option of the machinist. Accordingly, for cervical dowels, also referred to herein as anterior cervical fusion of ACF dowels, lengths of 8 mm, 9 mm, up to about 15 mm are desirable. Dowels of differing diameter are most conveniently obtained as follows:

| Diameter | Source |
| --- | --- |
| 10.6–11 mm | fibula |
| 12 mm | radius |
| 14 mm | ulna |
| 14+ mm | small humeri |

Dowels for thoracic and lumbar fusions, also referred to herein as anterior thoracic inner body fusion (ATIF) and anterior lumbar inner body fusion (ALIF) dowels, respectively, having a depth of between about 10–30 mm, and preferably between about 15–24 mm, are generally acceptable, depending on the needs of a particular patient. Dowels of differing diameter for thoracic and lumbar fusions are most conveniently obtained as follows:

| Diameter | Source |
| --- | --- |
| 14–16 mm | humerus |
| 16–18 mm | femur |
| 18–20 mm | tibia |

In every case, a consenting donor (i.e., a donor card or other form of acceptance to serve as a donor) is screened for a wide variety of communicable diseases and pathogens, including human immunodeficiency virus, cytomegalovirus, hepatitis B, hepatitis C and several other pathogens. These tests may be conducted by any of a number of means conventional in the art, including but not limited to ELISA assays, PCR assays, or hemagglutination. Such testing follows the requirements of: (i) American Association of Tissue Banks, Technical Manual for Tissue Banking, Technical Manual—Musculoskeletal Tissues, pages M19–M20; (ii) The Food and Drug Administration, Interim Rule, Federal Register/Vol. 58, No. 238/Tuesday, Dec. 14, 1993/Rules and Regulations/65517, D. Infectious Disease Testing and Donor Screening; (iii) MMWR/Vol. 43/No. RR-8, Guidelines for Preventing Transmission of Human Immunodeficiency Virus Through Transplantation of Human Tissue and Organs, pages 4–7; (iv) Florida Administrative Weekly, Vol. 10, No. 34, Aug. 21, 1992, 59A-1.001-014 59A-1.005(12) (c), F.A.C., (12)(a)–(h), 59A–1.005(15), F.A.C., (4)(a)–(8). In addition to a battery of standard biochemical assays, the donor, or their next of kin, is interviewed to ascertain whether the donor engaged in any of a number of high risk behaviors such as having multiple sexual partners, suffering from hemophilia, engaging in intravenous drug use etc. Once a donor has been ascertained to be acceptable, the bones useful for obtention of the dowels as desribed above are recovered and cleaned. The final machined product may be stored, frozen or freeze-dried and vacuum sealed for later use.

Since the dowels are obtained from transverse plugs across the diaphysis of long bones, each dowel has the feature of having the natural intra-medullary canal of the source bone forming a cavity through the dowel perpendicular to the length of the dowel. The canal cavity in the long bone is, in vivo, filed with bone-marrow. In the standard Cloward Dowel and unicortical dowels known in the art, no such natural cavity exists and the cancellous bone that forms the body of such dowels tends to be too brittle to accept machining of such a cavity. The instant dowels, by the nature of their origin, are already available with such a cavity. Naturally, based on this disclosure, those skilled in the art will recognize that other bone sources could be used which do not have the intra-medullary canal, and if sufficient strength is inherent to the bone, such a canal could be machined. Accordingly, such an extension of this invention should be considered as an obvious variant hereof and comes within the claims appended hereto. The marrow is removed from the intra-medullary canal of the diaphysial plugs and the cavity is cleaned. The cavity can then be packed with autogenous bone fragments from the recipient (i.e., when the cavity between adjacent vertebrae is formed, the removed bone fragments can be used as an autogenous packing), hydroxyapatite, BIOGLASS®, mixtures of these elements or any other osteogenic material to promote rapid fusion of the vertebrae between which the dowel is inserted. Bioactive glasses are generally composed of $SiO_2$, $Na_2O$, CaO, and $P_2O_5$. A preferred bioactive glass, BIOGLASS® 45S5 contains these compounds in the following respective weights: 45%, 24.5%; 24.4%, and 6%. As is evident from a review of *An Introduction to Bioceramics,* edited by Larry L. Hench and June Wilson (World Scientific Publishing Co. Pte. Ltd, 1993, volume 1), there is a vast array of bioceramic materials, including BIOGLASS®, hydroxyapatite and calcium phosphate compositions known in the art which can be used to advantage for this purpose. That disclosure is herein incorporated by reference for this purpose.

The method for preparing and using the diaphysial cortical dowel of this invention comprises the steps of obtaining a plug from the diaphysis of an appropriate donor bone. As desribed above, the donor will have been extensively screened for communicable diseases, cancer, and at-risk behavior prior to acceptance of the donor bone for dowel formation. The plug is then machined, preferably in a class 10 clean room, to the dimensions desired. The machining is preferably conducted on a lathe such as a jeweler's lathe or machining tools may be specifically designed and adapted for this purpose. Specific tolerances for the dowels and reproduceability of the product dimensions are important features for the successful use of such dowels in the clinical setting. Optionally, a groove 32 (see FIG. 3B) is inscribed on the cylindrical surface (circumference) of the dowel to prevent backing-out of the dowel, thereby forming a "rib" on the dowel which acts as a stop. Another option is to inscribe a thread 31 (see FIG. 3A) onto the circumference of the dowel. Machining of such grooves and threads on standard Cloward Dowels and even on unicortical dowels known in the art is difficult if not impossible due to the brittle cancellous nature of such dowels. Accordingly, the dowels of this invention have the advantage of having very good biomechanical properties amenable to such machining.

The forward end of the dowel which is to be inserted into a cavity formed between adjacent vertebrae is preferably chamfered by appropriate abrasive means known in the art such as machining, filing or sanding. The curvature of the chamfered end aids in the ease of insertion. The tolerance for the chamfering is fairly liberal and the desired object is merely to round or slightly point the end of the dowel that is to be inserted into the cavity formed between adjacent vertebrae to be fused.

Preferably, opposite the chamfered end, an instrument attachment hole is machined, for example by drilling and/or tapping. It is preferable that this end have a generally flat surface to accept the instrument for insertion of the dowel into the recipient. Preferably, the dowel will be of such dimensions as to fit standard insertion tools, such as those produced by Midas-Rex, Inc. In addition, it is preferred that a score mark be inscribed on the instrument attachment site of the dowel so that the surgeon can align the intra-medullary canal so that the canal is parallel with the length of the recipient's spinal column. With the aid of the score mark, once the dowel is inserted into the intervertebral cavity that is formed by the surgeon, and the canal is no longer visible, proper alignment is possible.

Referring to FIG. 1, there is shown, in FIG. 1A the standard unicortical dowel 100 known in the art, having a cortical surface 10, a drilled and/or tapped instrument attachment hole 15, and a body of brittle cancellous bone 20.

Figure 1B:
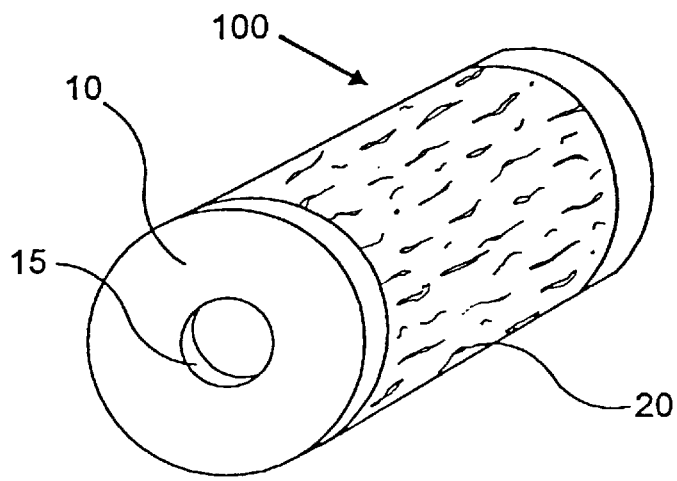
FIG. 1B depicts the structure of a standard Cloward Dowel known in the art.

In FIG. 1B, there is shown the standard bicortical dowel 200 known in the art having two cortical surfaces 10, a drilled and/or tapped instrument attachment hole 15, and a body of brittle cancellous bone 20.

Figure 1C:
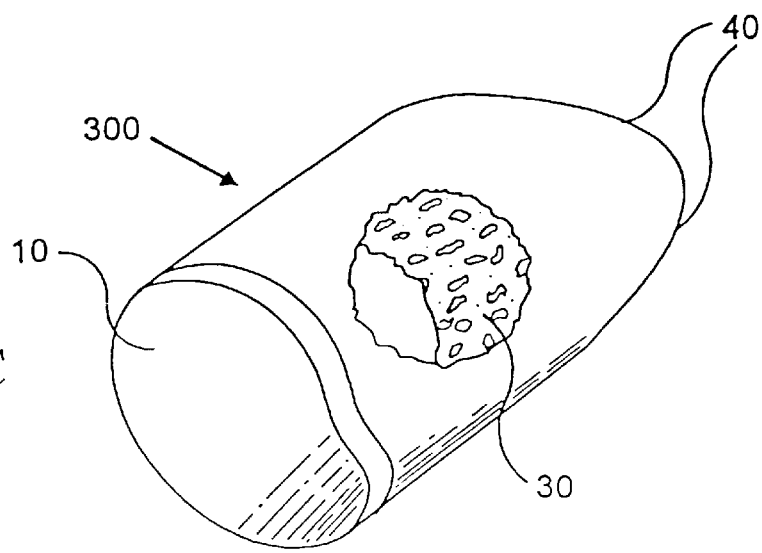
FIG. 1C depicts the structure of one embodiment of the diaphysial cortical dowel of this invention.

In FIG. 1C, one embodiment of the novel dowel 300 of this invention is shown having a cortical surface 10 into which an instrument attachment hole 15 and alignment score mark 16 may be machined (not shown as these elements are optional but preferred). Also shown is the intramedullary canal 30 and the chamfered insertion end 40 (also optional but preferred). Also not shown but easily inscribed due to the strength of the dowel 300 are circumferential (annular) ribbing or threads.

Figure 2B:
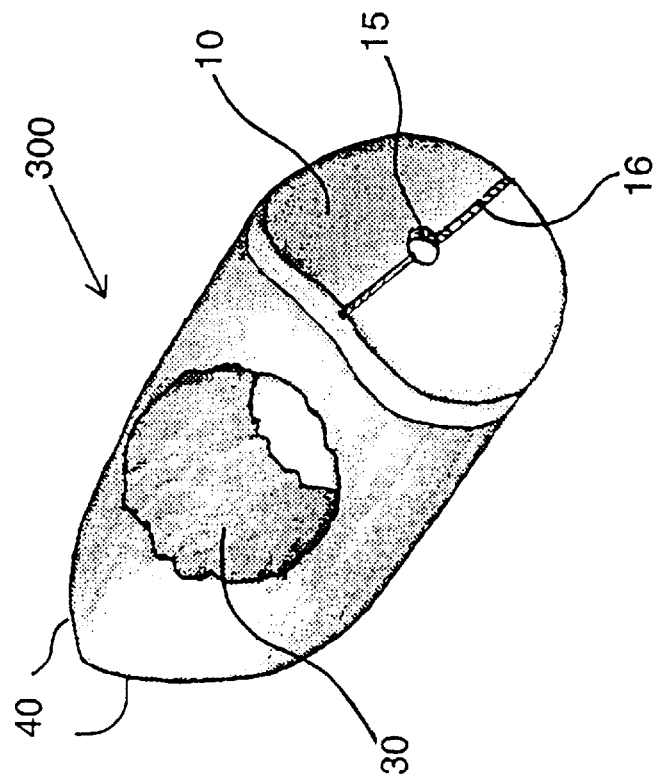
FIG. 2B depicts the ATIF or ALIF dowel with the instrument attachment hole and score mark.
Figure 2A:
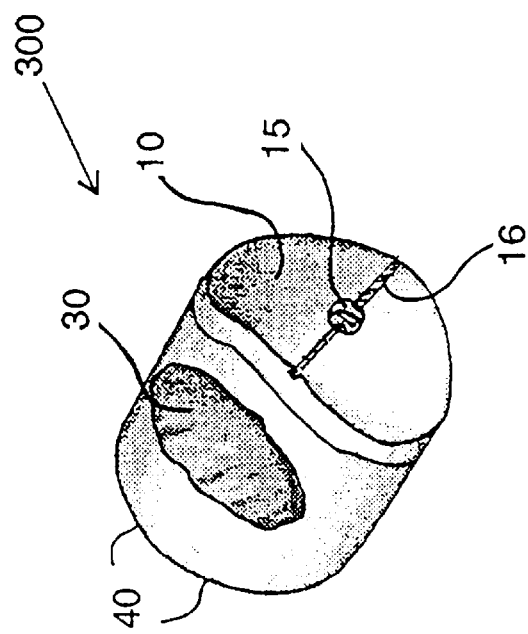
FIG. 2A depicts the ACF dowel with the instrument attachment hole and score mark.

Referring to FIG. 2, there is shown the ACF dowel in FIG. 2A and the ATIF or the ALIF dowel in FIG. 2B. Also shown, in addition to what is shown in FIG. 1, are the score mark 16 and the instrument hole 15.

Figures 3C, 3D:
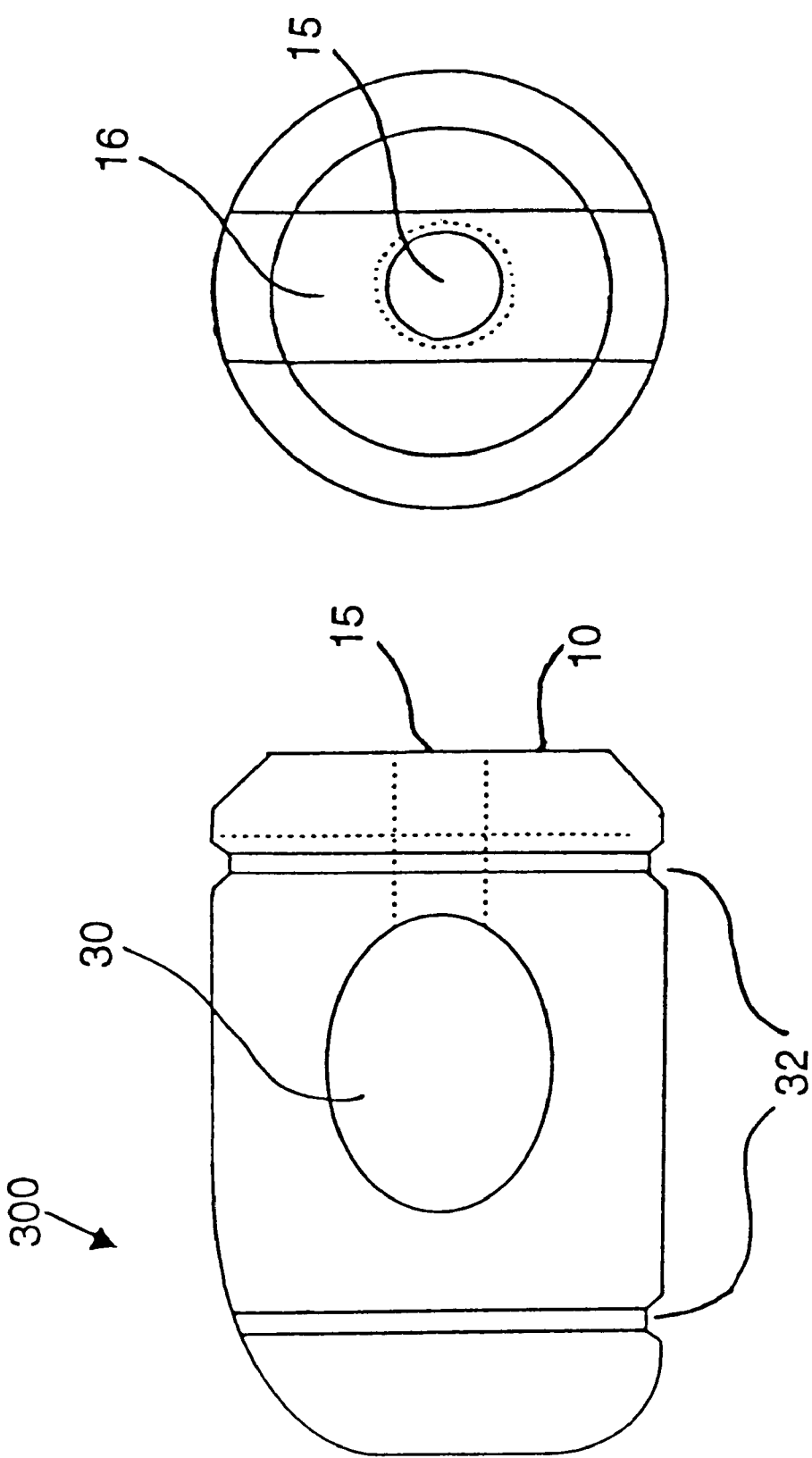
FIGS. 3C and 3D depict one embodiment of this invention in which the dowel is grooved.
Figure 4A:
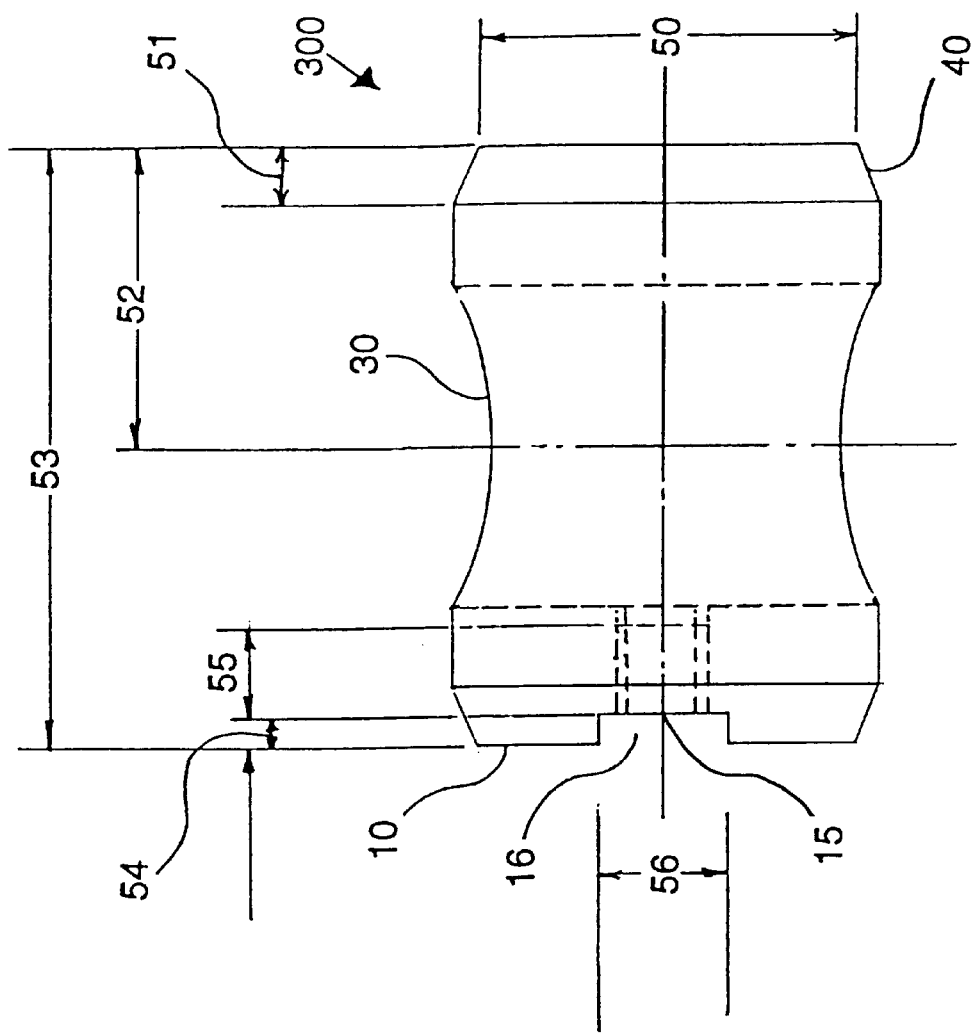
FIG. 4A is a side view of a dowel "blank" of this invention.
Figure 4B:
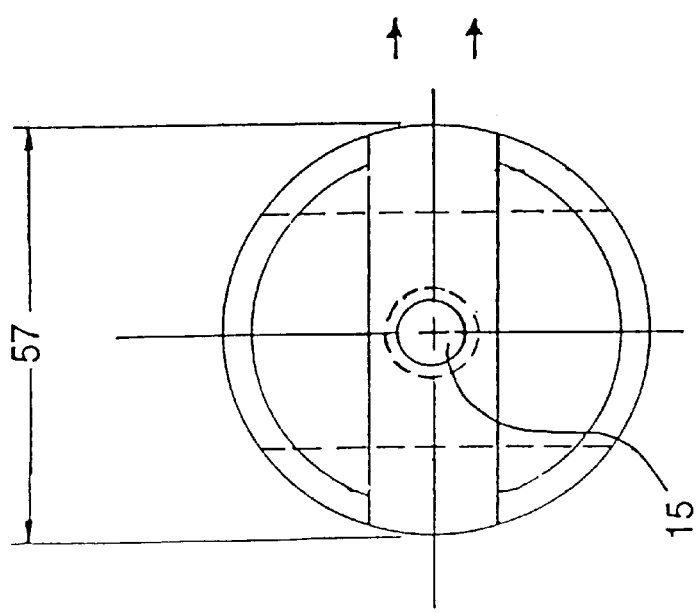
FIG. 4B is an end-on view of the dowel "blank".

In FIGS. 3A and 3B, the threaded 31 and grooved 32 dowel of this invention are shown. While those skilled in the art would know how to prepare a grooved or threaded dowel of this invention based on the foregoing disclosure and the disclosure of application Ser. No. 08/587,070, one specific technique for preparation of preferred embodiments of this invention is discussed herein. With reference to FIG. 4A, there is provided a side view of a diaphysial cortical dowel of this invention, which may be used as is, or which may be further machined to have grooves or threads. For purposes of illustration only, specific dimensions of dowel diameter, length and thread pitch are provided. Those skilled in the art will recognize that these specifics may be appropriately scaled, depending on the size of the dowel required for any given application.

In the schematic view provided in FIG. 4A, a blank dowel is represented which may be used to machine an 18 mm diameter by 28 mm length threaded dowel. Various features of the dowel blank are shown; the cortical bone 10, the tapped instrument attachment hole 15, the intra-medullary canal 30, and the chambered forward end of the dowel 40. For illustrative purposes, the following dimensions are also provided in inches and/or millimeters; 50—0.630" (16.0 mm); 51—0.100" (2.54 mm); 5.2—3.512" (26 mm) 54—0.50" (1.3 mm); 55—0.150" (3.8 mm); 56—0.217" (5.5 mm).

In FIG. 4GB, an end-on view of the dowel blank from the instrument-attachment hole 15 (rear) end of the dowel is provided. For illustrative purposes, the following dimensions are provided: 57—0.7087" (18 mm).

Figure 5B:
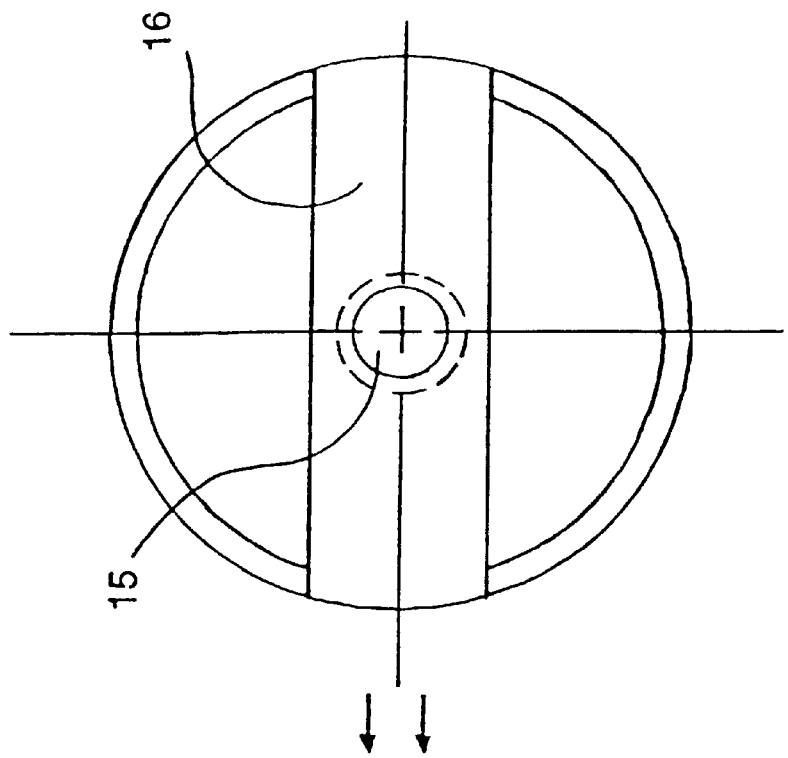
FIG. 5B is an end-on view of the threaded dowel.
Figure 5A:
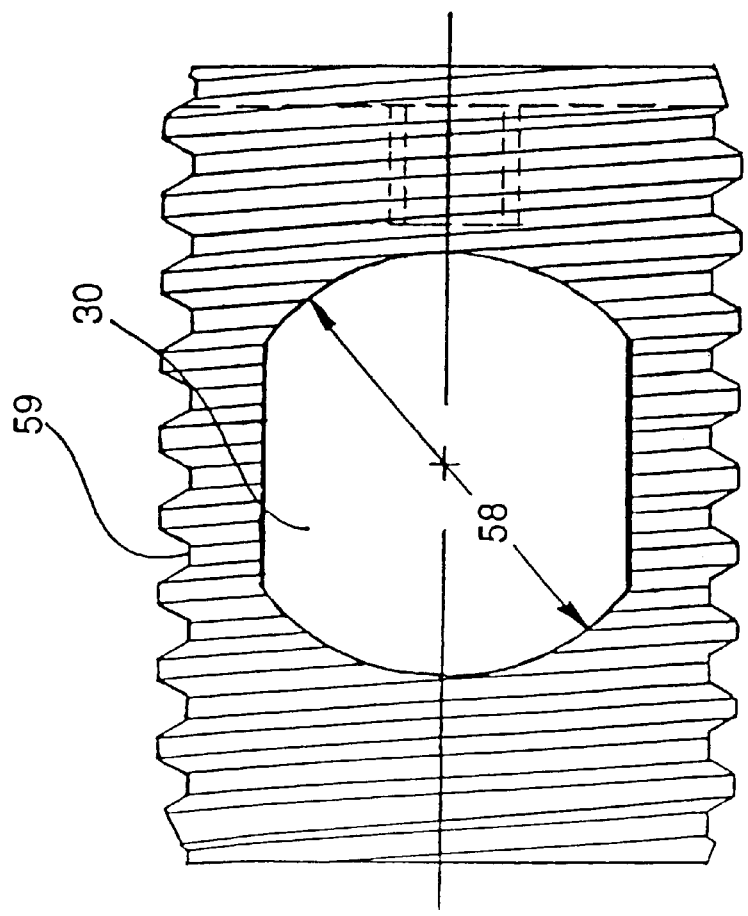
FIG. 5A is a threaded dowel of this invention.
Figure 5C:
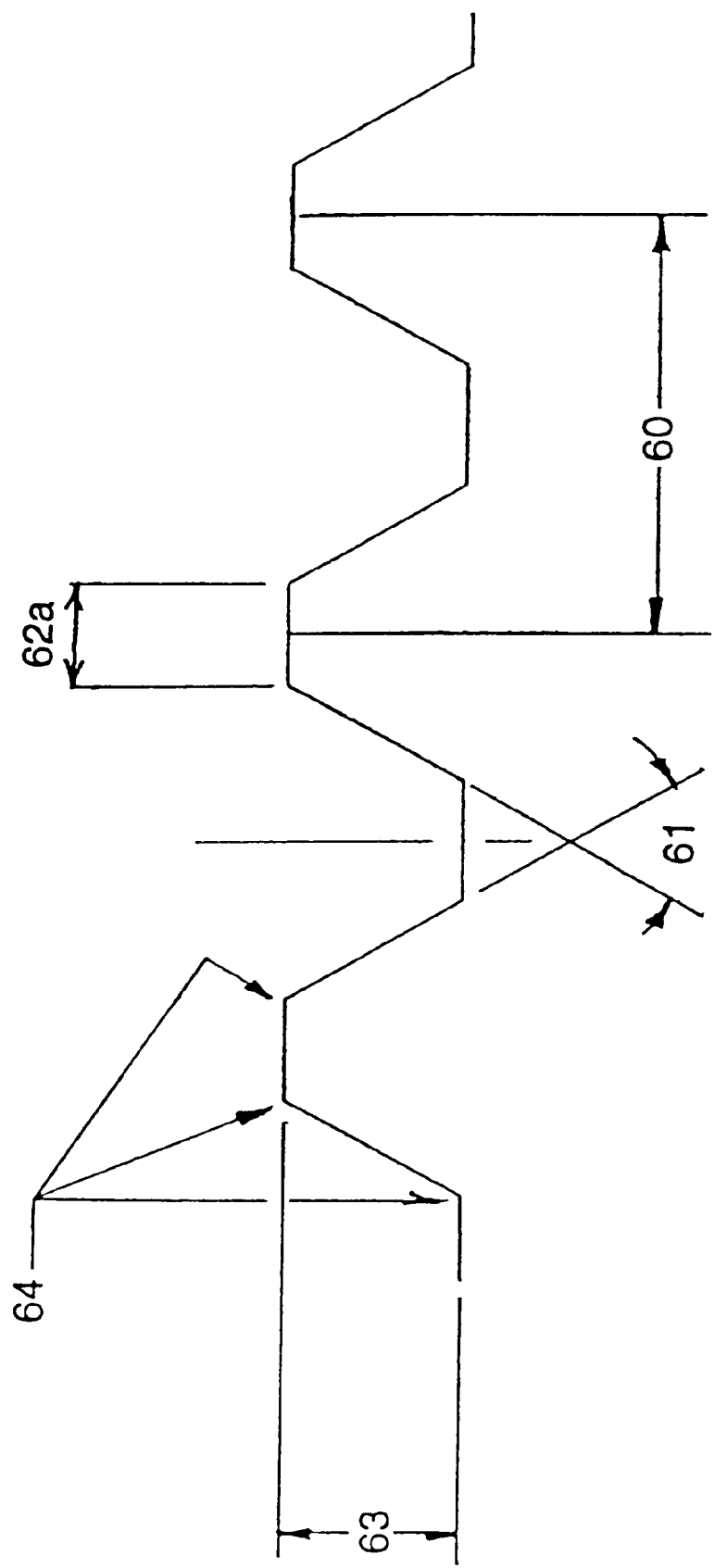
FIG. 5C is a detail of one embodiment of the thread of one embodiment of the threaded dowel of this invention.

In FIG. 5A, there is provided a view of the threaded dowel. For illustrative purposes, the following dimensions are provided:

For the intramedullary canal 30 a regular or irregular hole having a diameter 58 no greater than about 0.551" (14 mm) is preferred to avoid the walls of the dowel from being too thin, and so that a minimum wall thickness 59 at the root of the thread, on both sides of the canal, is preferably 4 mm or more. In FIG. 5B, an end-on view, from the orientation of the double arrows shown, shows the instrument attachment hole 15 and score mark 16 or driver slot 56. In FIG. 5C, there is shown a detail of one embodiment of the thread. In this embodiment, a right hand thread with ten threads per inch at a helix angle at the root diameter is about 2.8892° is provided as follows: the pitch 60—0.100" (2.5 mm); the thread angle 61—60°; the thread crest width 62a—0.025" (0.64 mm); the thread height 63 0.039" (1 mm); and the radius of the various thread angle as it changes 64 is typically about 0.010" (0.254 mm). Those skilled in the art will recognize that the foregoing specifics, while preferable, may be modified depending on the particular surgical requirement of a given application.

Figure 6A:
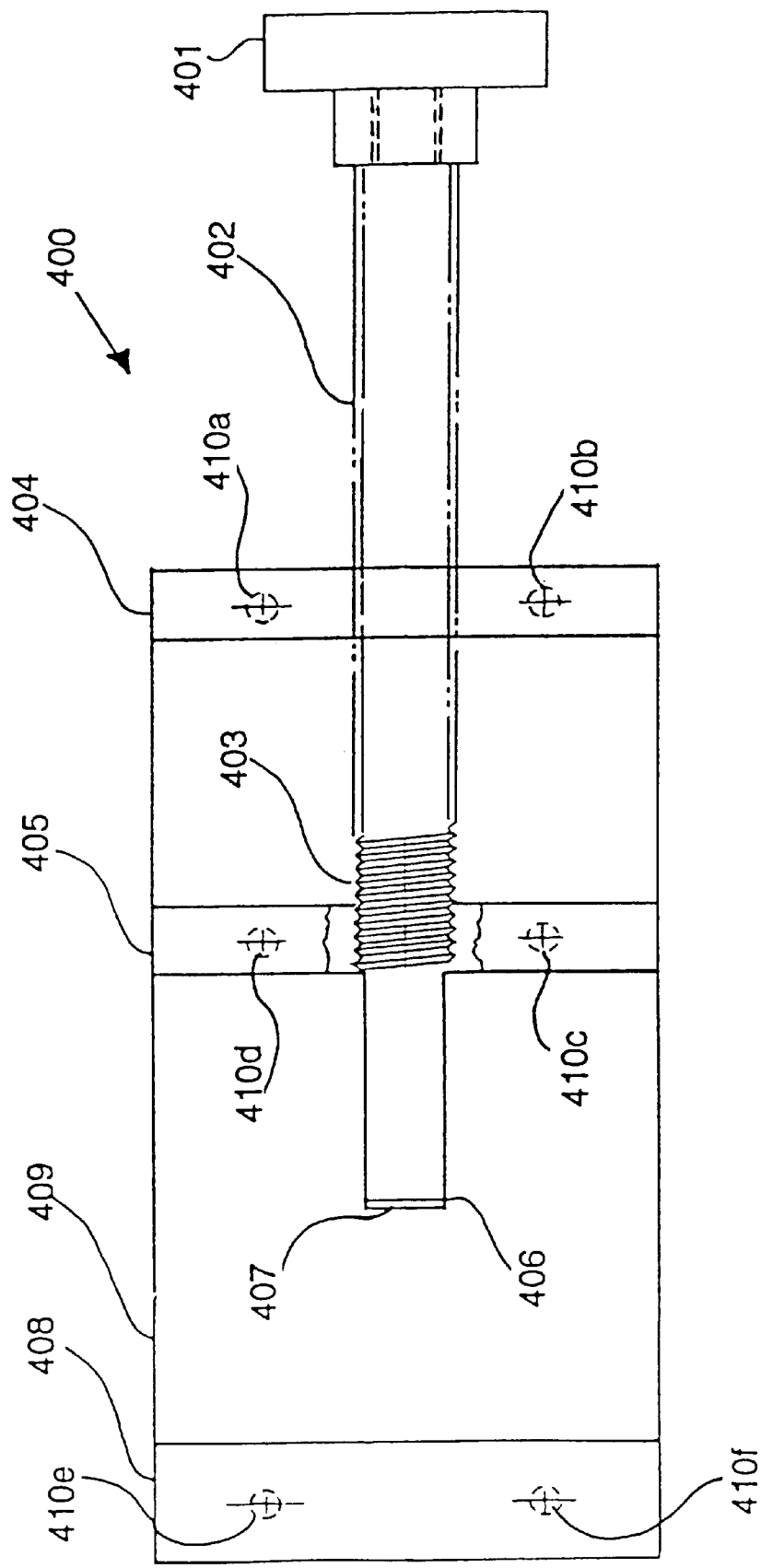
FIG. 6A is a top plan view of one embodiment of a dowel threader of this invention.

Those skilled in the art will also recognize that any number of different means may be employed to produce the threaded or grooved embodiments of the dowel of this invention. However, in one preferred embodiment, with reference to FIG. 6A, there is shown a top view of a thread cutter 400. In this embodiment, there is provided a handle 401 attached to a drive shaft 402 having a threaded portion 403 or a graduated segment means for controlled incremental advancement of the drive shaft 402 upon rotation of the handle 401. Support means 404 and 405 are provided for alignment and support of the shaft 402, with either or both support means having matching threads. (in this illustration, only support means 405 would have matching threads, while support means 404 would have a hole which may have bearings to assist in rotation of the handle 401 and shaft 402), or like graduated segment means for controlled incremental advancement of the drive shaft 402. At the terminal end 406 of the drive shaft 402, there is provided a protruding element 407 which corresponds in width to the driver slot 56 on the rear end of the dowel of this invention. At 408, there is provided a housing for the cutter assembly described further below. The supports 404 and 405 and the housing 408 for the cutter assembly are all mounted on a steady, solid, preferably weighty base unit 409 via screws, welding, or like attachment means at 410*a–f*.

Figure 6B:
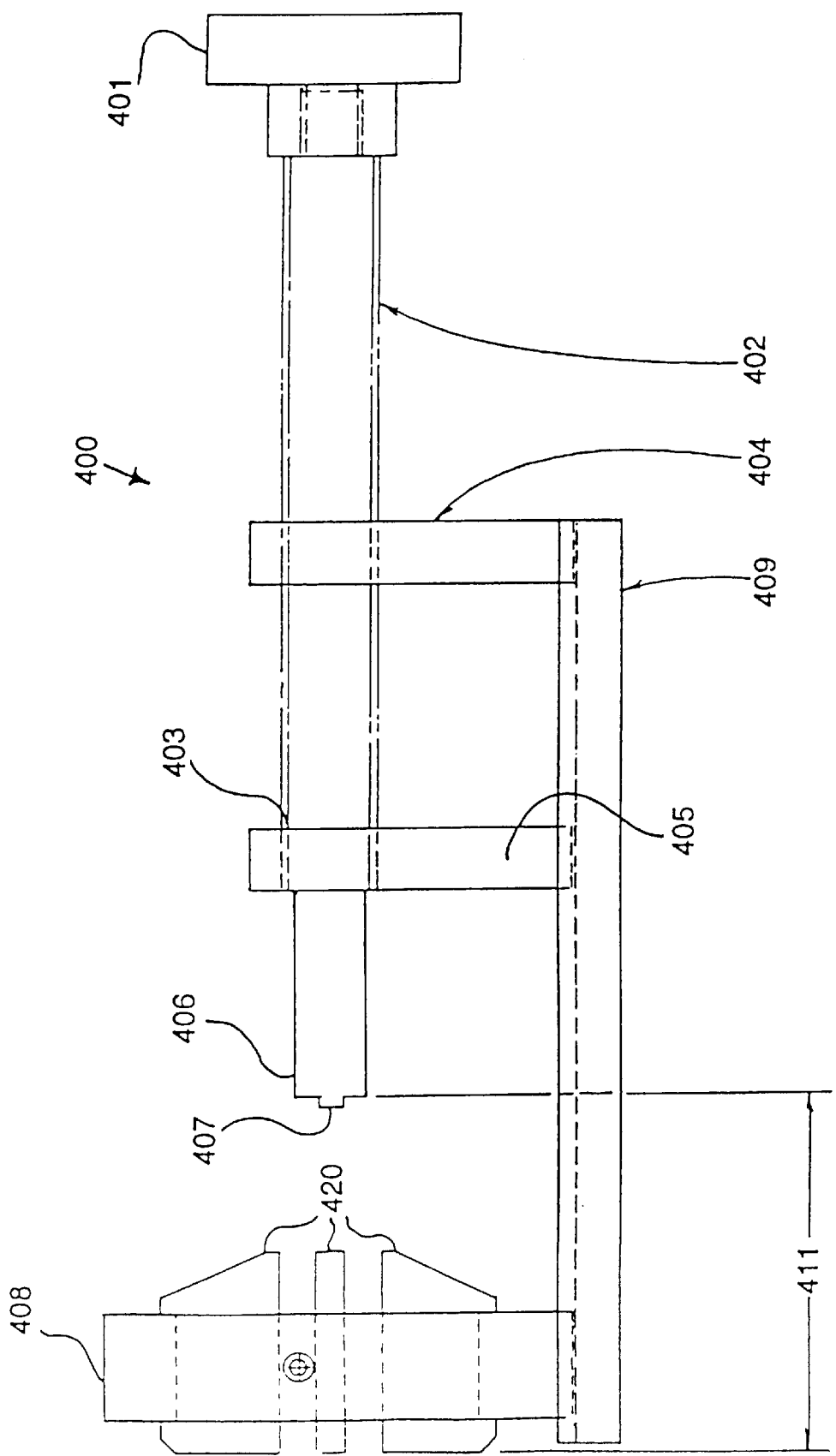
FIG. 6B is a side view of the dowel threader of this invention.

Referring now to FIG. 6B, there is provided a side view of this embodiment of the thread cutter 400, with like elements described above being similarly numbered. The following additional elements are evident from this view: cutter blades assembly 420 (comprising cutter blades 421 and 422 and guide plates 424 and 425, see FIG. 6C), is shown affixed to the cutter assembly housing 408, and an approximate travel distance 411 from the fully backed out terminal end of the drive shaft 406, to the end of the cutter assembly 420 is shown. This distance must be sufficient to allow insertion of a dowel blank and advancement of the blank through the cutter assembly 420 to allow a fully threaded dowel to emerge from the cutter assembly.

Figure 6C:
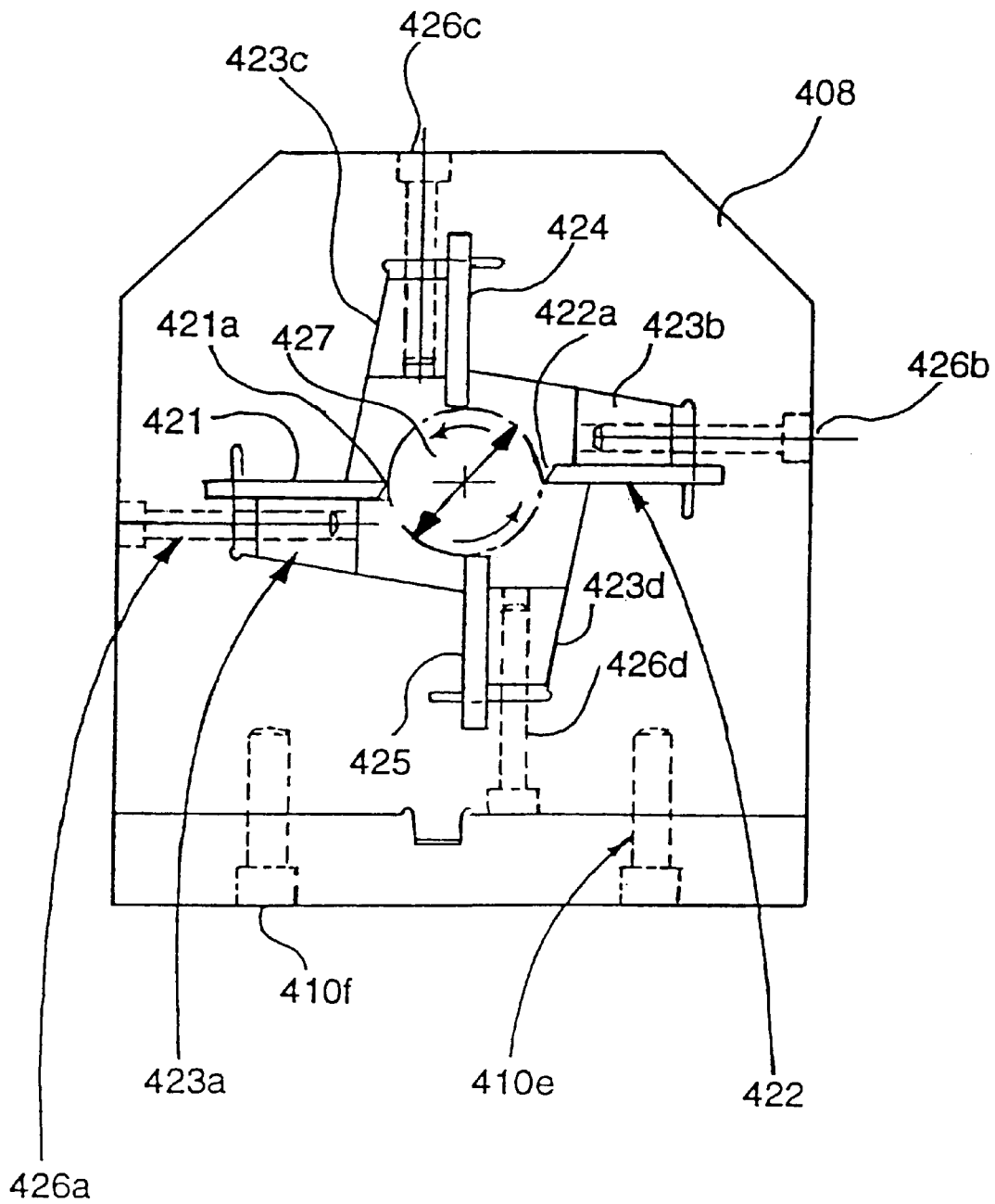
FIG. 6C is an end-on view of the dowel threader of this invention showing the elements of the cutter assembly.

In FIG. 6C, an end-on view (from the direction shown by the double arrows in FIG. 6B) of the cutter assembly 420 and cutter assembly housing 408 is provided. The elements of this embodiment of the cutter assembly are now desribed in further detail: corresponding 421 and 422 cutter blades are held in place in the housing 408 by fixation wedges 423*a* and 423*b* while guide plates 424 and 425, having no cutting teeth, are held in place by fixation wedges 423*c* and 423*d*. Fixation wedges 423*a–d* are held in place by screws 426*a–d*. The foregoing arrangement is preferred, as it allows for easy disassembly of the cutter assembly, removal of the cutter blades, cleaning of the various components, and if desired, sterilization by autoclaving chemical, irradiative or like means. It should be noted that the cutter blades 421 and 422 and guide plates 424 and 425 may be fixed in place by increasing the tension created by tightening screws 426*a–d*, which draws the fixation wedges 423*a–d* into the housing 408, thereby clamping these elements in place. Naturally, based on this disclosure, those skilled in the art will be able to develop equivalents of the cutter assembly system desribed herein, such as by use of wing-nuts, welding or like means to affix these various elements in appropriate cutting relationship to each other, without departing from the heart of this invention.

For purposes of illustration, the following additional features shown in FIG. 6C are noted: the diameter of the dowel that may be threaded according to this device is defined by the diameter of the aperture 427 created between the cutter blades 421 and 422 and the guide plates 424 and 425. It will be recognized by those skilled in the art that all of the foregoing elements should preferably be manufactured from durable materials such as 440 stainless steel or like materials. In particular, the cutting surfaces 421*a* and 422*a* of the blades 421 and 422, described in greater detail below, are made from hard metal. It should further be noted that the cutting edges 421*a* and 422*a* are disposed in relation to each other so that they are on axis.

With reference to FIG. 7, greater detail regarding the cutter blades 421 and 422 is provided: FIG. 7A provides a detail of the cutter, which maintains true tooth form from top to bottom, so that the cutter can be sharpened by surface grinding the face. This is achieved by wire-cutting the teeth such that there is about a 5° incline 62*c* between the descending vertices at the front and rear of each tooth, and about an 8° incline 62*d* between the front and rear of the top of each tooth. This aspect can best be seen in cutter blade end-on view 7B. Also, the thickness of the cutter blade: 62*e*, preferably about 0.100" (2.54 mm), can be seen in that figure.

Figure 7A:
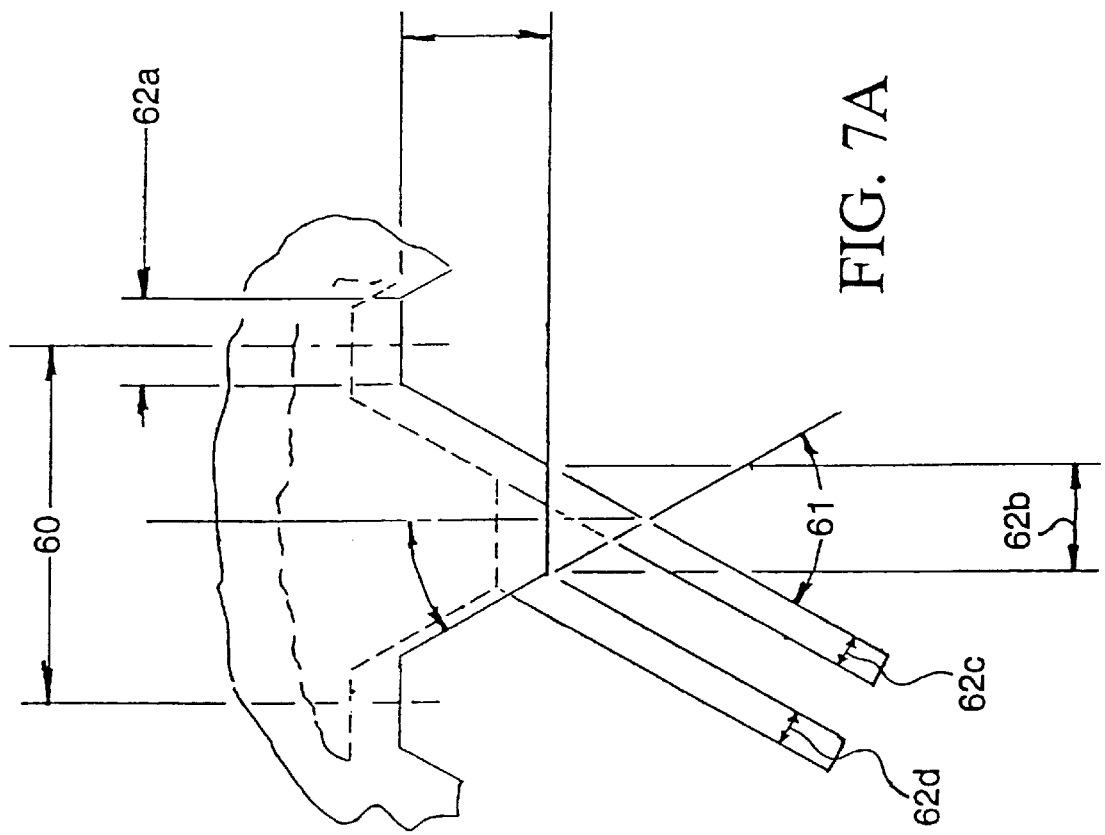
FIG. 7A is a detailed view of a single tooth of one cutter blade of the dowel threader.
Figure 7B:
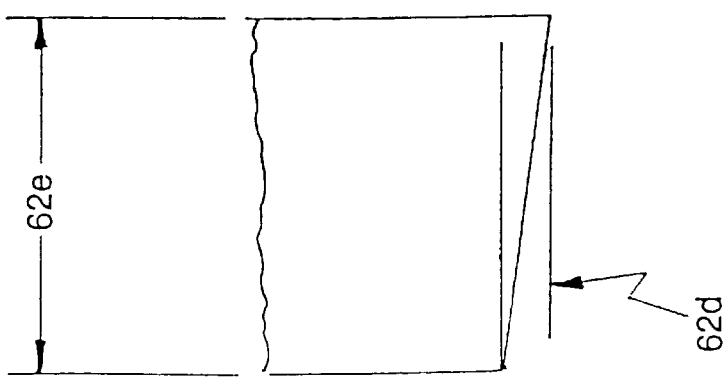
FIG. 7B is an end-on view of the tooth profile.
Figure 7C:
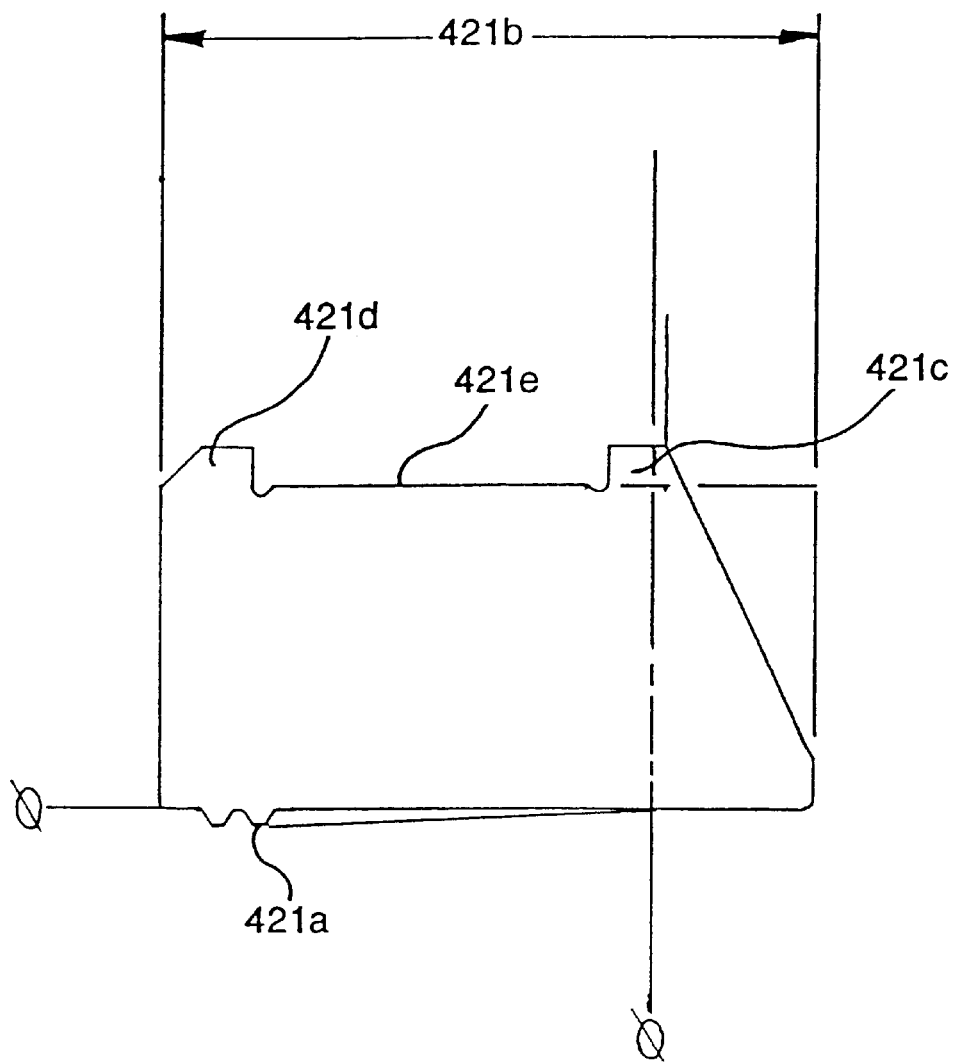
FIG. 7C is a global side view of a cutter blade.

As noted in FIG. 5C, the angle 61 in FIG. 7A is preferably about 60°. The width of the top of the tooth 62*b* is preferably about 0.025" (0.635 mm). The pitch 60 is preferably about 0.100" (2.5 mm). In FIG 7C, there is shown an overall view of the cutter blades 421 or 422 which are assembled in the cutter assembly housing 408. For illustrative purposes, the following dimensions are provided. The entire length of the cutter blade 421*b* is about 1.650" (4.2 cm). Fixation wings 421*c* and 421*d* are provided to allow proper seating of the cutter blade upon insertion into the housing 408. At Ø, a line is provided on cutter blades 421 and 422, which allows for appropriate registration between cutter blades 421 and 422 during manufacture thereof. Upon insertion into the housing 408, it is critical that the blades and the teeth thereon are appropriately registered so that as blade 421 cuts into the bone dowel as it is rotationally advanced through the cutter assembly 420, blade 422 is appropriately situated so that its matching teeth are in phase with the thread inscribed by the teeth on blade 421. This is accomplished by a combination of the fixation wings 421*d* and 421*c* properly seating in the hosing 408 such that the wall 421*e* abuts the housing 408 and the housing 408 walls about the insides of wings 421*d* and 421*c*.

Figure 7D:
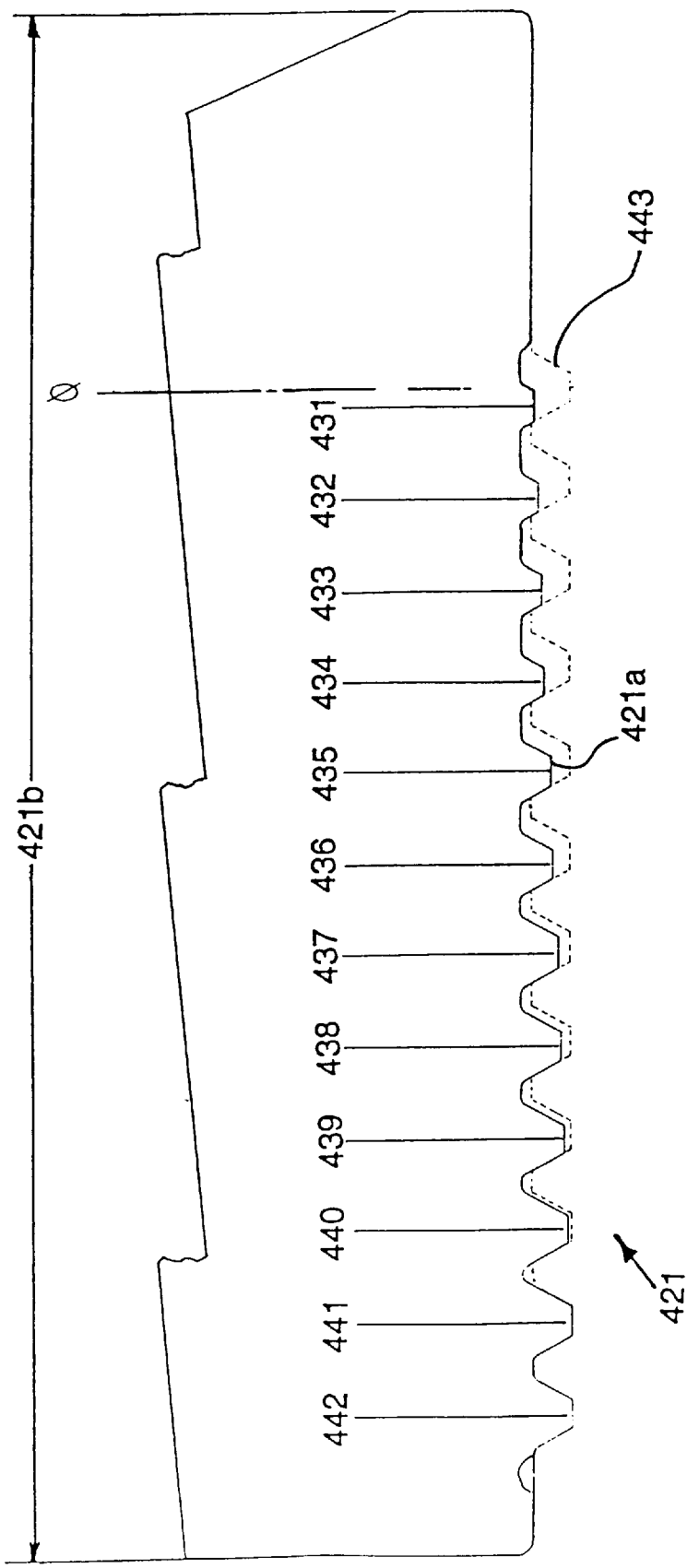
FIG. 7D is a detailed side view of cutter blade 421.
Figure 7E:
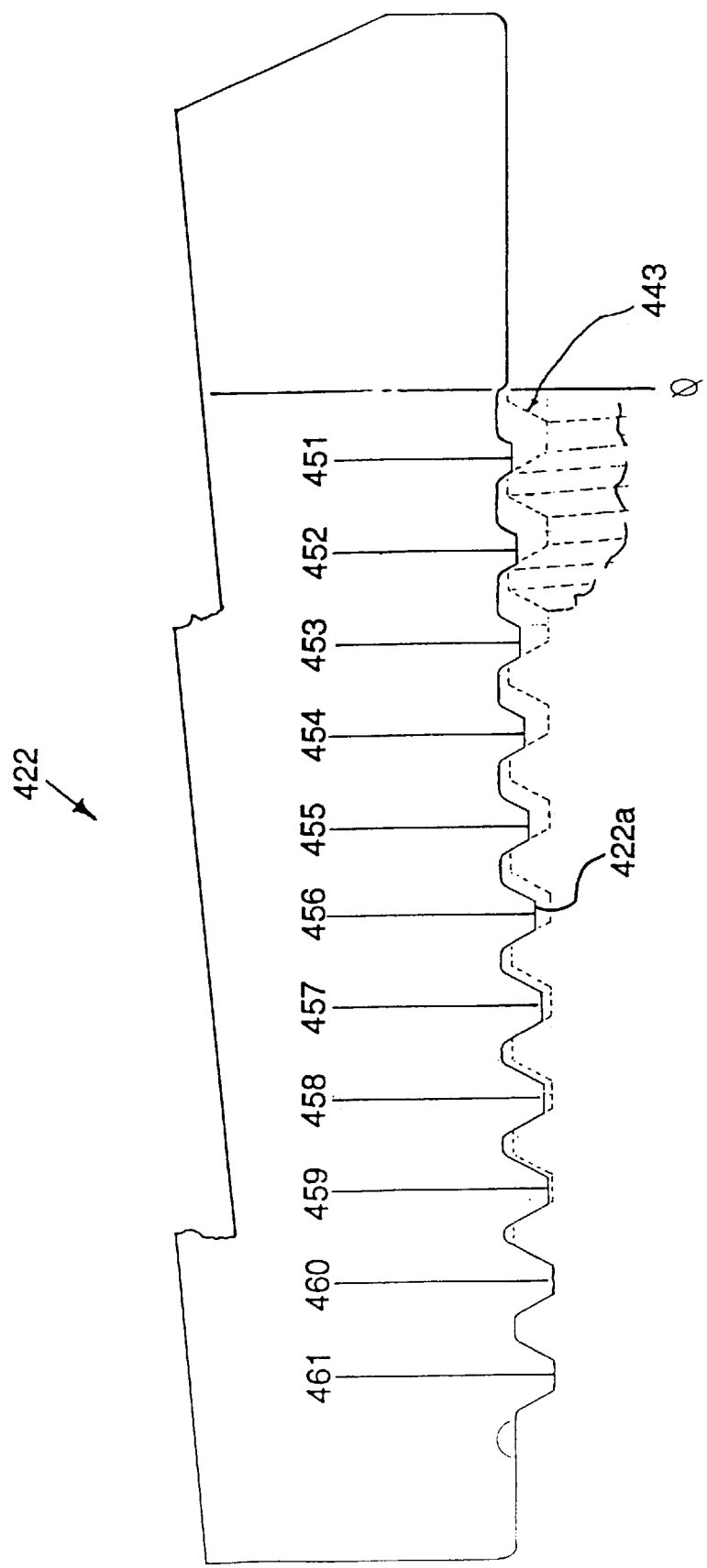
FIG. 7E is a detailed side view of cutter blade 422.

In FIG. 7D, there is provided a top view of cutting edge 421*a*. As can be seen, in this embodiment of the invention, the cutter blade 421 has twelve cutting teeth, numbered in the figure 431–442. As a dowel blank is fed into the cutter assembly, it first encounters a truncated tooth at 431, and at every subsequent tooth, the height of the tooth is incremented by about 0.004" (0.1 mm), starting from about 0.002" (0.5 mm) at 431, until the final tooth height is reached, in this example, of 0.039" (1 mm) at 441 and 442. The truncated teeth 431–440 feed into the dowel being cut along the 30° line so that the teeth cut on only two sides. The dotted line 443 shows that the final pitch and form that the cutter will cut in the bone dowel. Similar to the foregoing description for FIG. 7D above, the cutting edge 422*a* is shown in greater detail in FIG. 7E, with eleven teeth 451–461 spread over the length of the blade. At 451, the first tooth at 0.004" (0.1 mm) in this example is encountered by the blank and at each successive tooth, an increase of about 0.004" (0.1 mm) is made until the final tooth height of about 0.039" (1 mm) reached at 460 and 461. Again, the dotted line 443 shows the final pitch and form that the cutter will cut in the bone dowel.

In operation, based on the foregoing description, it will be appreciated that the cutter blades 421 and 422 are placed into the housing 408, clamped into place via the fixation wedges 423 and the screws 426, after the blades have been properly seated and the two blades are perfectly aligned. A blank dowel is then loaded into the orifice 427 and the drive shaft with the protruding element 407 is inserted into the driver slot 56 of the dowel 300. For this purpose, the score mark 16 may be matched as a groove (driver slot 56) which mates with the protruding element 407 such that rotational torque may be transmitted to the dowel. The groove may be oriented parallel to, perpendicular to, or at any other desired orientation with respect to the intramedullary canal of the dowel. The handle 401 is turned, forcing the dowel to rotate and advance incrementally through the cutter assembly 420, thereby inscribing the thread defined by the cutter blades 421 and 422 into the cylindrical surface (circumference) of the dowel.

As noted above, those skilled in the art will recognize that modifications to the specifics of the device described above will allow for the preparation of varied thread or grooves in the circumference of the dowel. For example, to form a groove in a dowel, the dowel could be mounted in a lathe, such as those known in the art and commercially available, for example from SHERLINE PRODUCTS INC. SAN MARCOS, Calif. 92069, and a cutter blade applied as the dowel is rotated.

According to the method of this invention, a dowel made from bone comprising a portion of the intra-medullary canal, is produced. The portion of the canal contained within the dowel of this invention may be treated to modify the shape, size, texture, and composition thereof, without departing from the scope of the invention disclosed and claimed herein. Any desirable external feature, including grooves, threads, cross-hatching, indentations, coatings and the like come within the scope of this invention and the appended claims.

Advantageously, the dowel of this invention may be conveniently incorporated into known fusion procedures. In one use, the surgeon creates a cavity between adjacent vertebrae that are to be fused, using conventional surgical procedures. The autogenous bone fragments produced in the formation of the cavity may be collected and packed into the intra-medullary canal of the diaphysial cortical dowel, or the dowel may be used with a pre-packaged osteogenic composition. A dowel of the appropriate dimensions is selected by the surgeon, based on the size of the cavity created and the needs of the particular patient undergoing the fusion. The dowel is mounted on an instrument via the instrument attachment hole and carefully inserted into the cavity created between the adjacent vertebra to be fused. For cervical fusions, only one dowel is needed. For lumbar fusions, two dowels may be required. In any event, the dowels may be applied laparoscopically using currently available instrumentation. Over a period of several months, it is found that substantial fusion of the adjacent vertebrae occurs.

While the foregoing description describes this invention, those skilled in the art will recognize that any of a number of variations on the basic theme disclosed herein can be made. Thus, for example, differing shapes can be made from the diaphysis of various bones and could be used for other orthopaedic purposes than vertebral fusions. In addition, any of a number of known bone treatments can be applied to the dowel of this invention to alter its properties. For example, the methods disclosed in U.S. Pat. Nos. 4,627,853; 5,053,049; 5,306,303; and 5,171,279 can be adapted and applied to the invention disclosed herein. Accordingly, the disclosures of those patents is herein incorporated by reference for this purpose.

Having generally described the dowel of this invention, its mode of manufacture and use, the following specific examples are provided.

EXAMPLE 1—BIOMEDICAL TESTING OF ACF DOWELS

Purpose: To describe the results from the compression testing of ACF dowels.

Materials: Instron Machine, ACF Dowels, Graph Recording Paper, Pen.

Procedure: The procedure utilized the above materials to compress the ACF dowels to failure and calculate their rupture modulus.

Preparing the dowel for compression:

Wipe the residual moisture from the surface of the dowel.

Set Instron for desired full scale load, crosshead speed, and paper speed.

Position dowel under compression head with hole up.

Testing procedures:

Start the graph paper to record the composition load.

Start the Instron to compress the dowel.

Stop and release the load when failure is achieved or the machine is at a maximum compression load and the dowel does not fail.

Results: The dowels were all compressed to failure. The results from the testing is included in the data below.

| Maximum Load | Minimum Load | Mean Load | Median |
|---|---|---|---|
| 383 kg | 200 kg | 267.14 kg | 264 kg |
| 3743 Newtons | 1960 Newtons | 2618 Newtons | 2587 Newtons |

EXAMPLE 2—BIOMECHANICAL TESTING OF ATIF & ALIF DOWELS

Purpose: To describe the results from the compression testing of the ATIF & ALIF dowels.

Materials: Instron Machine, ATIF & ALIF Dowels, Graph Recording Paper, Pen.

Procedure: The procedure utilized the above materials to compress the dowels to failure and calculate their rupture modulus.

Preparing the dowel for compression:

Wipe the residual moisture from the surface of the dowel.

Set Instron for desired full scale load, crosshead speed, and paper speed.

Position dowel under compression head with hole up.

Testing procedures:

Start the graph paper to record the composition load.

Start the Instron to compress the dowel.

Stop and release the load when failure is achieved or the machine is at a maximum compression load and the dowel does not fail.

Results: The ATIF & ALIF dowels were tested in the above manner and did not fail with a compression load of 500 kg (4900 Newtons). This is the Instron's maximum load.

EXAMPLE 3—CERVICAL FUSION USING DIAPHYSIAL CORTICAL DOWEL

Preoperative Diagnosis. Ruptured cervical disc and spondylosis C5-6.

Postoperative Diagnosis. Same.

Operative Procedure. Anterior cervical discectomy and fusion C5-6.

After satisfactory general endotrachael anesthesia in the supine position, the patient was prepped and draped in the routine fashion. Incision was made in the skin length of the neck and carried through the platysma muscle. Dissection was carried down to expose the anterior vertebral column and the appropriate space identified by x-ray. Discectomy and foraminotomy were then performed and there was found a central, extruded fragment of disc toward the right side. When adequate decompression had been achieved, a bone dowel was cut from bone bank fibula and counter-sunk between the vertebral bodies to afford distraction. The wound was then irrigated with Bacitracin and closed in layers with Dexon and steri strips.

Postoperative evaluation and subsequent patient monitoring revealed successful operative outcome and good vertebral fusion.

It should be understood that the examples and embodiments desribed herein are for illustrative purposes only and that various modifications or changes in light thereof will be suggested to persons skilled in the art and are to be included within the spirit and purview of this application and the scope of the appended claims.

REFERENCES

U.S. Pat. No. 5,015,247
U.S. Pat. No. 4,627,853
U.S. Pat. No. 5,053,049
U.S. Pat. No. 5,306,303
U.S. Pat. No. 5,171,279
University of Florida Tissue Bank, Inc. Allograft Catalog.
An Introduction of Bioceramics, Hench, Larry L., June Wilson (eds.), World Scientific Publishing Co. Pte. Ltd., volume (1993)
Bone Graft Surgery in Disease, Injury and Deformity, Albee, D. Appleton-Century Company, Inc. (1940)
Vich, *J. Neurosurg.* 63:750–753 (1985)
Vich, U.S. Pat. No. 4,877,020

In considering the claims which follow, reference is made to the disclosure of U.S. Pat. No. 4,950,296, wherein a combination bone grafting unit is disclosed comprising: a cortical shell having a selected outer shape wherein a cavity is formed therein, into which a cancellous plug is inserted. Per the instant invention, a cortical dowel, graft or threaded dowel is provided wherein a portion of the intra-medullary canal of a bone is included in the device to provide a canal running through the device, into which osteogenic material may be packed.

What is claimed is:

1. A cortical dowel, graft or threaded bone dowel (300) which comprises a generally cylindrical dowel characterized in that it comprises cortical bone having a canal through the dowel generally perpendicular to the long axis of the dowel, wherein said canal is defined by the intra-medullary canal of the donor's bone (30).

2. The cortical dowel, graft or threaded bone dowel (300) of claim 1 comprising a bone plug obtained from the diaphysis of a long bone having an intra-medullary canal (30).

3. The cortical dowel of claim 2 having a chamfered end (40).

4. The cortical dowel of claim 3 wherein the end opposite the chamfered end has an instrument attachment hole machined therein (15).

5. The cortical dowel of claim 4 wherein the end having the instrument attachment hole also has a score mark or drive slot (16) machined therein.

6. The cortical dowel of claim 5 further comprising an external feature, (31, 32) machined into the cylindrical surface (circumference) of the dowel.

7. The cortical dowel of claim 6 wherein said feature includes a groove (32).

8. The cortical dowel of claim 6 wherein said feature includes threads (31) formed along a portion of the length of the dowel.

9. The cortical dowel of claim 1 having a depth of between about 8 mm and about 30 mm.

10. The cortical dowel of claim 9 having a diameter of between about 10 mm and about 24 mm.

11. The cortical dowel of claim 2 further comprising an osteogenic composition packed within said canal (30).

12. The cortical dowel of claim 11 wherein said osteogenic composition is autogenous bone, hydroxyapatite, bioactive glass, a calcium phosphate ceramic or a mixture of these.

13. The cortical dowel of claim 1 obtained as a transverse plug from the shaft of a donor's fibula, radius, ulna, humerus, femur or tibia.

14. A method of making a dowel which comprises machining a transverse plug from the diaphysis of a donor's fibula, radius, ulna, humerus, femur or tibia, said plug having a diameter of between about 10 mm and about 24 mm and a depth (length) of between about 8 mm and about 30 mm characterized in that said dowel has, running through it, perpendicular to the long axis of the dowel, the intra-medullary canal (30) of the donor's bone.

15. The method of claim 14 further comprising chamfering one end of said plug to form a generally curved surface for ease of inserting of the dowel into an intervertebral cavity.

16. The method of claim 14 further comprising machining an instrument attachment hole (15) into the end of the dowel opposite the chamfered end.

17. The method of claim 16 further comprising inscribing a score mark or driver slot (16) on the instrument attachment end of the dowel to allow for proper alignment of the intra-medullary canal or further machining of the dowel.

18. The method of claim 14 further comprising inscribing a groove (16) into the end of said dowel wherein said groove mates with a drive shaft for driving said dowel through a cutter assembly for machining an external feature into the circumference of the dowel.

19. The method of claim 18 wherein said cutter assembly comprises a set of registered cutter blades (421, 422) with teeth of incremental height (431–442, 451–461), such that as the dowel is rotationally driven through said cutter assembly, said external feature is inscribed into the circumference of the dowel.

20. The method of claim 18 wherein said external feature is a thread (31).

21. The method for fusing vertebrae which comprises making a cavity between the vertebrae to be fused and inserting therein a diaphysial cortical dowel (300) having an intra-medullary canal (30) running through said dowel perpendicular to the long axis of said dowel.

22. The method of claim 21 further comprising retaining bone fragments obtained during the making of said cavity between said vertebrae to be fused and packing said bone fragments into the intramedullary canal (30) of said diaphysial cortical dowel (300).

23. The method of claim 21 further comprising packing the intra-medullary canal of the diaphysial cortical dowel with an osteogenic composition.

24. The method of claim 23 wherein said osteogenic composition is autogenous bone, fragments obtained during the making of said cavity between said vertebrae to be fused, a bioceramic, bioactive glass, hydroxyapatite, calcium phosphate or a combination of these.

25. The cortical dowel of claim 1 prepared by a process comprising machining a transverse plug from the diaphysis of a donor's fibula, radius, ulna, humerus, femor or tibia, said plug having a diameter of between about 10 mm and about 24 mm and a depth (length) of between about 8 mm and about 30 mm such that the resulting dowel has, running through it, perpendicular to the long axis of the dowel, the intra-medullary canal (30) of the donor's bone.

26. The cortical dowel of claim 25 wherein said process of preparation further comprises chamfering one end of said plug to form a generally curved surface for ease of insertion of the dowel into an intervertebral cavity.

27. The cortical dowel of claim 26 wherein said process of preparation further comprises machining an instrument attachment hole (15) into the end (10) of the dowel opposite the chamfered end (40) and inscribing a score mark (16) on the instrument attachment end of the dowel to allow for proper alignment of the intra-medullary canal (30).

28. The cortical dowel of claim 25 wherein said process of preparation further comprises machining an external feature (31, 32) into the cylindrical surface (circumference) of the dowel.

29. The cortical dowel of claim 28 wherein said feature includes a groove (32).

30. The cortical dowel of claim 28 wherein said feature includes threads (31) formed along a portion of the length of the dowel.

31. The cortical dowel of claim 30 wherein said thread has a pitch of about 0.1" (mm).

32. The graft (300) according to claim 1 comprising a body consisting of cortical bone, said body having a longitudinal axis along a length of said body and defining a canal (30) therethrough along a second axis substantially perpendicular to said longitudinal axis.

33. The graft of claim 32 wherein said graft has a cross-sectional diameter perpendicular to said longitudinal axis that is substantially uniform along said length of said body.

34. The graft of claim 32 further comprising an external feature (31, 32) machined into the circumference of the graft.

35. The graft of claim 34 wherein said feature includes a groove (32).

36. The graft of claim 34 wherein said feature includes threads (31) formed along a portion of the length of the dowel.

37. The cortical dowel of claim 36 wherein said thread has a pitch of about 0.1" (2.54 mm).

38. The graft of claim 32 further comprising an osteogenic composition packed within said canal (30).

39. The graft of claim 38 wherein said osteogenic composition is autogenous bone, hydroxyapatite, bioactive glass, a calcium phosphate ceramic or a mixture of these.

40. A threaded bone dowel according to claim 1 prepared by machining the bone dowel with an apparatus for cutting a thread in a bone dowel which comprises:

(a) a handle (401) for rotating a shaft (402), the distal end (406) of which is adapted (407) to matably engage a driver slot (16) in one end of said dowel;

(b) a support means (404, 405) for said shaft wherein said support means comprises a graduated segment (403) for controlled incremental advancement of a drive shaft (402) which passes through said support means and wherein said drive shaft also has a graduated segment which matches said graduated segment in said support means such that, upon rotation of said handle, rotation and incremental advancement of the distal end of said shaft into a cutter assembly (420) occurs due to engagement of the matching graduated segments of said support means and said drive shaft; and (c) a cutter assembly (420), fixed in position in relation to said support means, having at least two opposing cutting surfaces (421, 422) which, in register with each other, inscribe a thread on the cylindrical surface (circumference) of a bone dowel matably driven by said end of said rotating shaft.

41. A method for fusing vertebrae which comprises making a cavity between the vertebrae to be fused and inserting therein the threaded bone dowel of claim 40.

* * * * *